United States Patent [19]
Creemer et al.

[11] Patent Number: 5,480,906
[45] Date of Patent: Jan. 2, 1996

[54] STEREOCHEMICAL WORTMANNIN DERIVATIVES

[75] Inventors: Lawrence C. Creemer; Herbert A. Kirst, both of Indianapolis, Ind.

[73] Assignee: Eli Lilly and Company, Indianapolis, Ind.

[21] Appl. No.: 269,716

[22] Filed: Jul. 1, 1994

[51] Int. Cl.$^6$ .................... A61K 31/365; C07D 311/78
[52] U.S. Cl. ............................... 514/453; 549/275
[58] Field of Search .................... 549/275; 514/453

[56]  References Cited

U.S. PATENT DOCUMENTS

| | | | |
|---|---|---|---|
| 3,668,222 | 6/1972 | Hauser | 549/275 |
| 4,988,682 | 1/1991 | Kozikowski | 514/150 |

OTHER PUBLICATIONS

Yano, Hiroshi, et al., *Journal of Biological Chemistry*, vol. 268 (34), pp. 25846–25856 (1993).
Kimura, K., et al., *Ninth Annual Meeting on Oncogenes*, Abstract: p. 203 (1993).
Matter, W. F., et al., Biochem. Biophys. Res. Commun., 186(2): pp. 624–631 (1992).
Haeflinger, W., et al., *Helv. Chem. Acta*, 56(8): pp. 2901–2904 (1973).
MacMillan, J., et al., *J. Chem. Soc.* Perkin I, pp. 2892–2898 (1972).
Abbas, H. K., et al., *Appl. Environ. Microbiol.*, 54(5): pp. 1268–1274 (1988).
Shibasaki, F., et al., *J. Biol. Chem.*, 266(13): pp. 8108–8114 (1991).
Nakanishi, S., et al., *J. Biol Chem.*, 267(4): pp. 2157–2163 (1992).
Ohara–Imaizumi, M., et al., *Biochem. Biophys. Res. Commun.*, 185(3): pp. 1016–1021 (1992).
Kaplan, D. R., et al., *Cell*, 50: pp. 1027–1029 (1987).
Valius, M., et al., *Cell*, 73: pp. 321–334 (1993).
Coughlin, S. R., et al., *Science*, 243: pp. 1191–1194 (1989).
Baggiolini, M., et al., *Exp. Cell Res.*, 169: pp. 408–418 (1987).

*Primary Examiner*—C. Warren Ivy
*Assistant Examiner*—Ba K. Trinh
*Attorney, Agent, or Firm*—Thomas J. Dodd; David E. Boone

[57]  ABSTRACT

This invention relates to derivatives of Wortmannin and particularly to 11,17 substituted derivatives of Wortmannin. The invention also relates to a method of using these compounds as PI-3-kinase inhibitors and as anti-tumor agents.

35 Claims, No Drawings

5,480,906

1

STEREOCHEMICAL WORTMANNIN DERIVATIVES

FIELD OF THE INVENTION

This invention relates to Wortmannin derivatives, and will have application to stereochemical alcohol and ester derivatives, and to a method of using these derivatives to inhibit PI-3-kinase activity and to treat certain malignant tumors.

BACKGROUND OF THE INVENTION

Wortmannin is a known potent inhibitor of phosphotidylinositol-3-kinase (PI-3-kinase), and has been suggested for use as a potential anti-cancer agent. Wortmannin is a naturally occurring compound isolated from culture broths of the fungus Penicillium wortmannin and has the following basic structure:

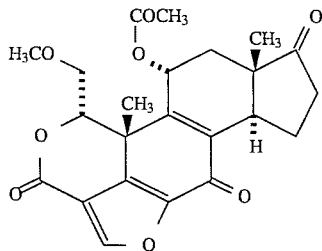

One of the disadvantages of wortmannin is its toxicity to living creatures. Even in low dosages, wortmannin in pure form was often lethal to laboratory animals. Attempts to synthesize derivatives of wortmannin have so far been problematical.

SUMMARY OF THE INVENTION

The present invention provides for wortmannin compounds which exhibit enhanced potency for PI-3-kinase inhibition and have probable use as anti-cancer agents. The compounds of the present invention include 11-substituted, 17-substituted and 11, 17 disubstituted derivatives of wortmannin. Generally, these derivatives include 11-esters as their base substitution groups, but other like compounds will no doubt exhibit similar activity. The general formula for the compounds of this invention is:

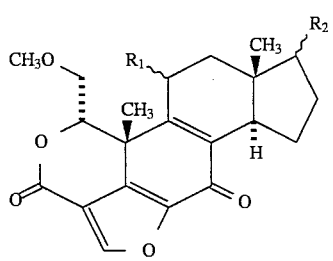

wherein $R_1$ is $$\overset{O}{\underset{\|}{\text{—}}},$$

or $OR_3$;

$R_2$ is $$\overset{O}{\underset{\|}{\text{—}}},$$

or $OR_3$;

each R3 individually is hydrogen, arylacyl, $C_3$–$C_8$ acyl or substituted acyl; and when $R_1$ is $$\overset{O}{\underset{\|}{\text{—}}}$$

or OH, $R_2$ is not $$\overset{O}{\underset{\|}{\text{—}}}.$$

The present invention also provides for a method of inhibiting PI-3-kinase activity in mammals by administration of an effective amount of one of the compounds of this invention. Since PI-3-kinase activity has been suggested as a factor in certain types of cancer, the invention also provides for use of the compounds as anti-cancer (anti-tumor) agents, and also for pharmaceutical formulations which includes the compound in combination with a pharmaceutically acceptable carrier, excipient or diluent.

It is therefore a principal object of this invention to provide for new compounds which are derived from the wortmannin family.

Another object is to provide for the use of the compounds as PI-3-kinase inhibitors, and as anti-tumor agents.

Other objects will become apparent upon a reading of the following description.

DETAILED DESCRIPTION OF THE INVENTION

The term "$C_1$–$C_{16}$ alkyl" represents a straight or branched alkyl chain having from one to sixteen carbon atoms. Typical straight or branched $C_1$–$C_{16}$ alkyl groups include methyl, ethyl, n-propyl, isopropyl, n-butyl, isobutyl, sec-butyl, t-butyl, n-pentyl, isopentyl, n-hexyl, 2 methylpentyl, n-octyl, decyl and the like. The term "$C_1$–$C_{16}$ alkyl" includes within it the terms "$C_1$–$C_4$ alkyl", "$C_1$–$C_6$ alkyl", and $C_1$–$C_{10}$ alkyl.

The term "$C_3$–$C_8$ acyl" represents a $C_2$–$C_7$ alkyl group attached to a carbonyl group. Typical acyl groups include propionyl, butylryl, valeryl, and caprolyl. Arylacyl represents an acyl group attached to a terminal aryl moiety as those two terms are defined elsewhere in this specification. Substituted acyl represents an acyl group as defined above and having non-alkyl moieties or additional bonds attached to the alkyl carbon chain. Examples of substituted acyl as described below include N,N-dimethylaminoacetyl, acryloyl and chloroacetyl.

The term "carboxy protecting group" as used herein refers to one of the ester derivatives of the carboxylic acid group while reactions are carried out on other functional groups. Examples include methyl, ethyl, benzyl, 4-nitrobenzyl, 4-methoxybenzyl, 3,4-dimethoxybenzyl, 2,4-dimethoxybenzyl, 2,4,6-trimethoxybenzyl, 2,4,6 trimethylbenzyl, benzhydryl, t-butyl, t -amyl, trityl, trimethylsilyl, t-butyldimethylsilyl, alkyl, 1-(trimethylsilylmethyl)-prop- 1-en-3-yl, and the like.

The term "aryl" represents an aromatic moiety. Examples include phenyl, and polynuclear aromatic moieties, such as naphthyl, fluorenyl, anthracyl and phenanthryl. The term "substituted aryl" represents an aryl group substituted with one or more moieties chosen from the group consisting of halogen, hydroxy, cyano, nitro, $C_1$–$C_6$ alkyl, $C_1$–$C_4$ alkoxy, carboxy, acetyl, formyl, carboxymethyl, hydroxymethyl, amino, aminoethyl or trifluoromethyl. Examples of substituted aryl groups include 4-methylphenyl, 2-methylphenyl, 4-methoxyphenyl, 4-(i-propyl)phenyl, 4-cyclopentylphenyl, 4-( 1,1,4,4-tetramethylbutyl)phenyl, 4-acetylphenyl, 4-trifluoromethylphenyl, 4-chlorophenyl, 2-bromophenyl, 3-iodophenyl, 6-bromonaphthyl, 3,4-methylene-dioxyphenyl, indenyl, 1,2,3,4 tetrahydronaphthyl, and 1,2,4,4-tetramethyl- 1,2,3,4-tetrahydronaphthyl.

The term "arylalkyl" represents a $C_1$–$C_4$ alkyl group bearing an aryl group. Representatives of arylalkyls include benzyl, 1-phenylethyl, 2-phenylethyl, 3-phenylpropyl, 4-phenylbutyl, 2-methyl-2 phenylpropyl, 4-(chlorophenyl) methyl, (2,6-dichlorophenyl)methyl, (4-hydroxyphenyl)methyl, (2,4-dinitrophenyl)methyl or the like.

The present invention provides for a series of novel compounds derived from the naturally occurring compound wortmannin. The molecular structure of wortmannin is as follows:

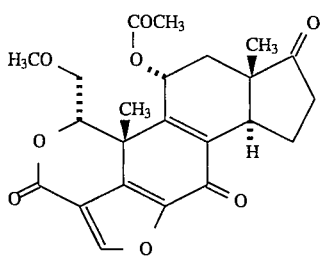

The compounds of this invention primarily include 11,17 Oxy-substituted derivatives. The derivative compounds are preferably esters and/or ethers, but will include all of those compounds which have the general formula:

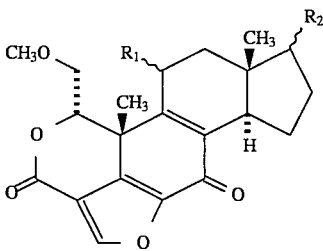

wherein:

$R_1$ is $$\overset{O}{\underset{\|}{\phantom{C}}},$$

or $OR_3$;

$R_2$ is $$\overset{O}{\underset{\|}{\phantom{C}}},$$

or $OR_3$;

each $R_3$ individually is hydrogen, arylacyl, $C_3$–$C_8$ acyl or substituted acyl; and when $R_1$ is $$\overset{O}{\underset{\|}{\phantom{C}}}$$

or OH, $R_2$ is not $$\overset{O}{\underset{\|}{\phantom{C}}},$$

or a pharmaceutically acceptable salt thereof.

While all of the formula (I) compounds are believed to possess the ability to inhibit the action of PI-3-kinase, certain compounds are preferred. The preferred compounds have the general formula:

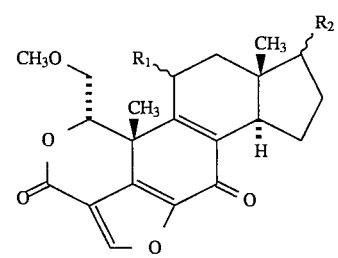

(Ia)

wherein $R_1$ is $$\overset{O}{\underset{\|}{\phantom{C}}},$$

or $OR_3$;

$R_2$ is $$\overset{O}{\underset{\|}{\phantom{C}}},$$

or $OR_3$; and $R_3$ is hydrogen, $C_3$–$C_8$ acyl or substituted acyl.

In the most preferred compounds from this group of preferred compounds $R_1$=O—$C_3$–$C_8$ acyl or O-substituted $C_3$–$C_8$ acyl; and $$R_2 = \overset{O}{\underset{\|}{\phantom{C}}},$$

or OH, all of the compounds are synthesized from wortmannin using procedures which will be described in detail below. It is understood that these procedures are merely indicative and introduced for purposes of explanation, not to be seen as limiting the invention to the steps and specific compounds described.

11-desacetyl derivatives of wortmannin are first prepared by methods well known in the art according to the following scheme I.

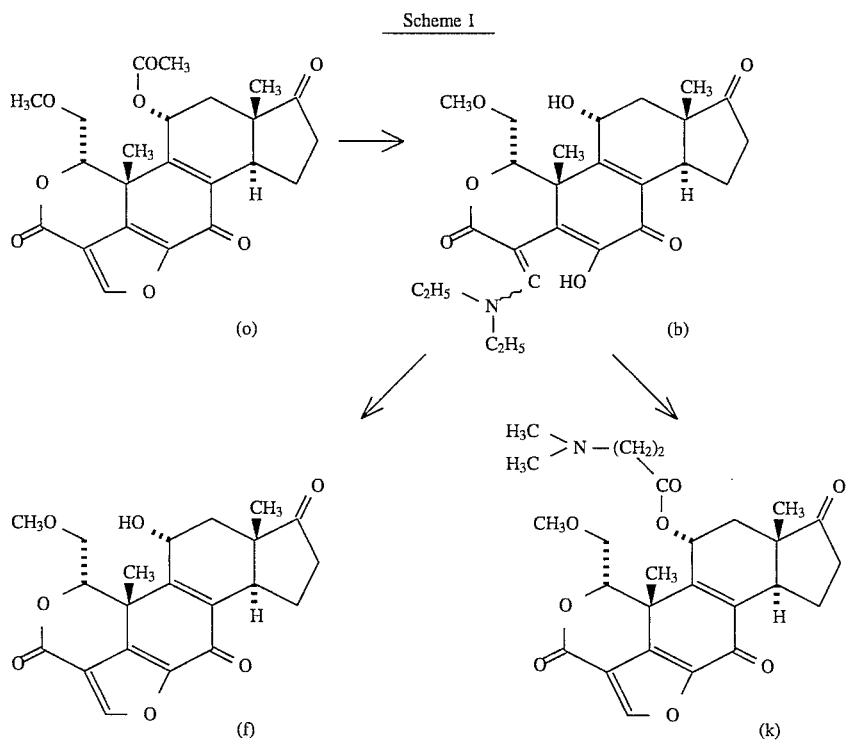

Scheme I

In the general scheme, wortmannin (o) is suspended in solvent and reacted with an amine to yield the open ring compound (b). Compound (b) generally does not show significant ($IC_{50}$>10 ng/ml) activity as a PI-3-kinase inhibitor. Compound (k) is prepared from (b) by reaction with a tertiary amine and an acryloyl halide then with dimethylamine, and reformation of the furan ring with a strong acid in solvent. Compound (f) is prepared by reacting compound (b) with a strong acid in the presence of a solvent. Purification of compounds (k) and (f) is carried out by well known methods.

Compound (f) exhibits 50% inhibition vs. PI-3-kinase at 10 ng/ml. The most preferred compounds are produced directly or indirectly from compound (f) according to the following Scheme II:

Scheme II
Scheme IIa
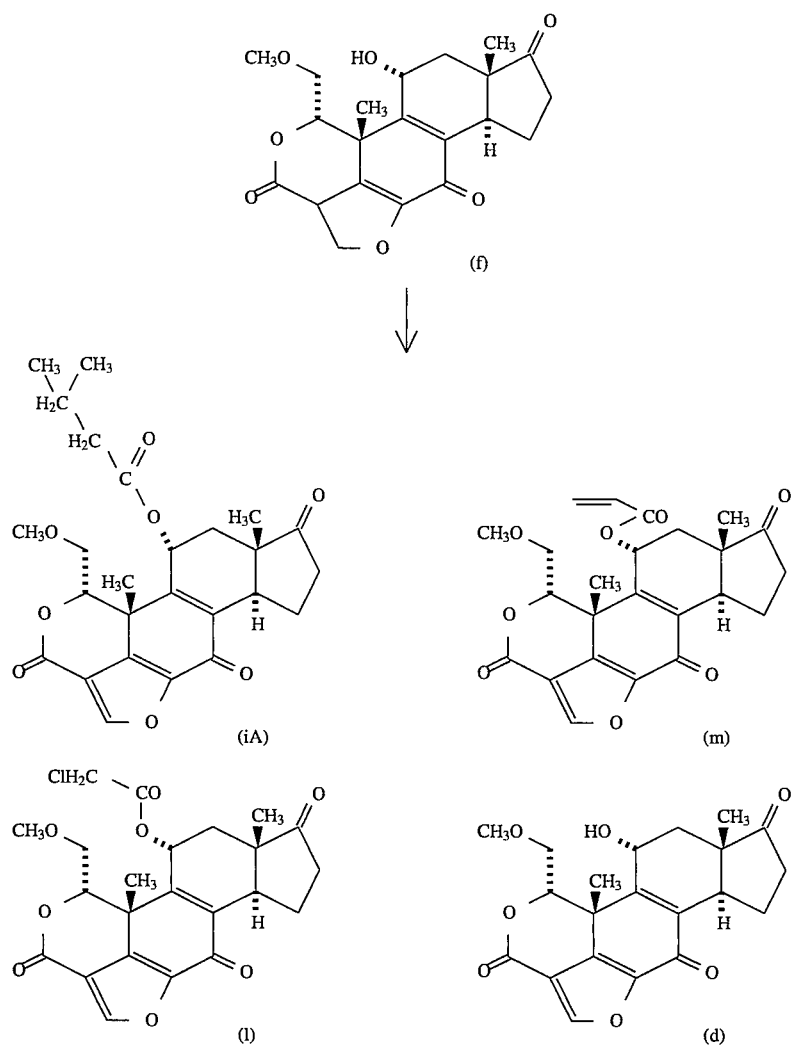
Scheme IIb
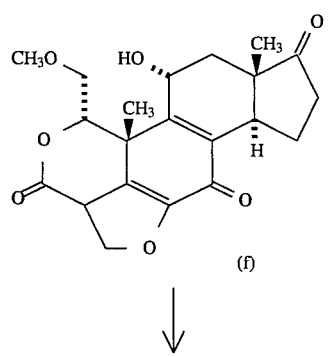

-continued
Scheme II
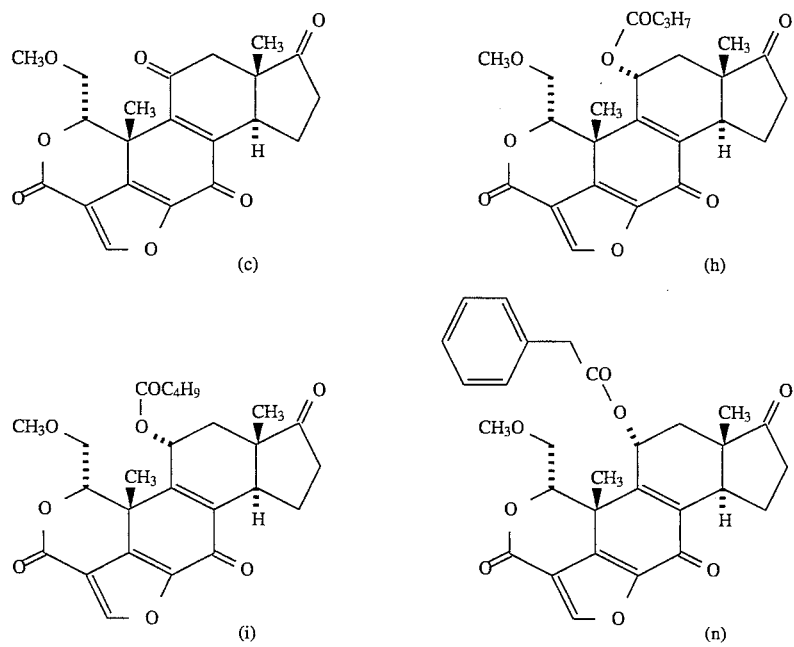
Scheme IIc
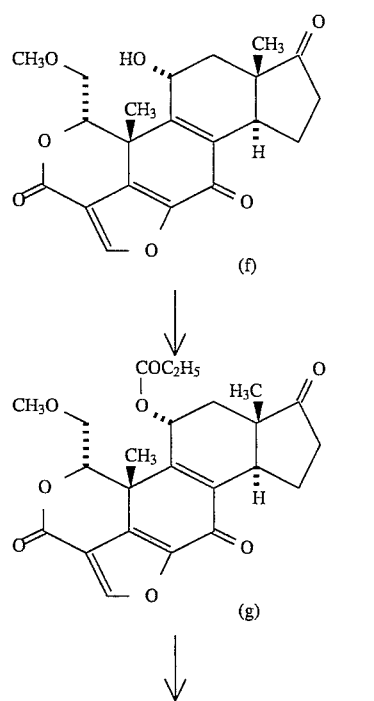

-continued
Scheme II

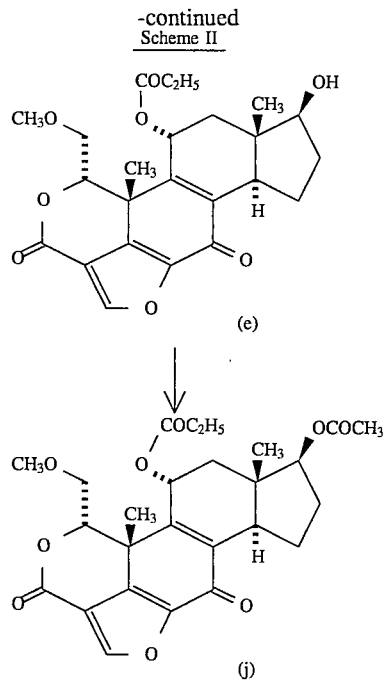

According to the above scheme, preferred compounds (g), (h) and (i) are prepared directly from compound (f) by reaction with the corresponding acid anhydride to produce the 11-substituted wortmannin esters. The isovaleryl derivative (iA) is prepared from (f) by reaction with an isovaleryl halide. Compound (c) is prepared by reacting (f) with an oxidizing agent to form the 11-oxy derivative. Compound (d) is prepared by reducing the 17-oxy group of (f) to a hydroxy.

Compound (n) is prepared by reacting (f) with a phenylacetoxy halide. Compound (l) is prepared by reacting (f) with a chloroacetyl halide, and (m) by reacting (f) with an acyloxyl halide.

Finally, compound (e) is formed by reduction of (g), and (e) may then be reacted with an acid anhydide to form compound (j). A detailed description of the procedures outlined above is presented later in this specification.

The present invention also provides for the use of the compounds as inhibitors of PI-3-kinase. In order to demonstrate the activity of the compounds of this invention, the following experiments were performed:

Purification of Phosphatidylinositol 3-Kinase

PI 3-kinase may be prepared by multiple methods. In one method, PI 3-kinase was prepared from confluent Swiss 3T3 cells obtained from the American Type Culture Collection, Rockville, Md. Prior to purification of PI 3-kinase, cells were maintained in bulk culture in Dulbecco's Modified Eagles Medium (DMEM; Sigma, St. Louis, Mo.) supplemented with 10% fetal calf serum and were passaged using 0.25% trypsin and 0.02% ethylenediaminetetracetic acid (EDTA). $24 \times 10^6$ cells on four, 100 mm culture plates were washed with 10 mL Hanks Balanced Salt Solution (HBSS; Sigma) pH 7.4, and the cells were left in DMEM without fetal calf serum for 1 hour before being stimulated for 15 minutes with 100 ng/mL of the recombinant human BB homodimer of platelet derived growth factor (PDGF; Genzyme, Cambridge, Mass.). The medium was aspirated and the cells washed with 10 mL of HBSS before being lysed with 3 mL of 137 mM NaCl, 20 mM of Tris (pH 8.0) containing 1 mM of $MgCl_2$, 10% of glycerol, 1% of Triton X-100 (Rohm and Haas, Philadelphia, Pa.), 2 µg/mL of leupeptin, 2 µg/mL of aprotonin, 1 mM or phenylmethylsulfonyl fluoride (PMSF), and 1 mM of sodium orthovanadate. The cells were scraped free from the surface of the dish and centrifuged at 6,000 x g for 10 minutes. The supernatant was mixed with 50 µL of washed IgG2bk antiphosphotyrosine antibody beads (Upstate Biotechnology Inc., Lake Placid, N.Y.) in 1.5 mL tubes. The tubes were capped and rotated for 2 hours at 4° C. and the beads were twice washed with 1 mL of HBSS containing 2 µg/mL of leupeptin, 4 µg/mL of aprotonin, 1 mM of PMSF, 200 µM of adenosine, and 1 mM of sodium orthovanadate. The tyrosine phosphorylated PI 3-kinase was eluted from the beads with 200 µL/tube of 10 mM Tris (pH 7.5), 2M of NaCl, 1 mM of EDTA, 200 µM of adenosine, and 10 mM of sodium phenylphosphate.

In another, preferred, method, PI 3-kinase was prepared from bovine brain. Two bovine brains (wet weight about 900 g) were obtained from a local slaughterhouse within minutes of slaughter, packed on ice, and homogenized within one hour. Brains were trimmed of excess fat and blood vessels and then homogenized using a Tekmar Tissuemizer (Cincinnati, Ohio) at 4° C. in 20 mM of Tris(pH 8.3) containing 250 mM of sucrose, 6 mM of β-mercaptoethanol, 1 µg/ml of leupeptin, 1 µg/ml of pepstatin A, 0.4 mM of PMSF, and 1 mM of $MgCl_2$.

Following centrifugation for 60 minutes at 10,000 x g, the pH of the supernatant (about 1200 mL) was lowered to 5.75 using dropwise addition of 1M acetic acid at 4° C. After stirring for an additional 15 minutes at 4° C., the solution was centrifuged for 60 minutes at 13,500 x g. The supernatant was discarded. Pellets were resuspended in Buffer A (20 mM of Tris, pH 8.3, containing 6 mM of β-mercaptoethanol, 0.1 mM of ethylene glycol-bis(β-aminoethyl ether) N,N,N', N'-tetraacetic acid (EGTA), 1 µg/mL of leupeptin, 1 µg/mL of pepstatin A, and 1 mM of $MgCl_2$), and loaded onto a Fast Flow Q Sepharose column (300 ml) at a flow rate of 5 mL/min at 4° C. After loading, the column was washed with 3 volumes of Buffer A containing 0.1M of KCl and the kinase was then eluted with a linear gradient of Buffer A/0.1M KCl to Buffer A/0.6M KCl at 3 mL/min over 7 volumes.

Fractions were assayed for PI 3-kinase activity using 10 µL of the fraction and phosphatidylinositol as substrate as described below. PI 4-kinase eluted in the breakthrough; PI 3-kinase eluted at approximately 0.3M of KCl. The PI 3-kinase pool was subjected to a 40% ammonium sulfate precipitation. Following centrifugation (60 minutes at 13,500 x g), pellets were resuspended in Buffer B (10 mM of potassium phosphate, pH 7.4, containing 6 mM of β-mercaptoethanol, 1 µg/mL of leupeptin, 1 µg/mL of pepstatin A, and 1 mM of $MgCl_2$), and loaded onto a 50 mL hydroxylapatite column (Calbiochem, Inc., La Jolla, Calif.) at 2.5 mL/minute. The column was washed with 150 mL Buffer B until the $A_{280}$ baseline reached zero, and the kinase was then eluted with a linear gradient of 10–320 mM of $KH_2PO_4$ at 1 mL/minute over 450 minutes.

Active fractions were pooled and then loaded at 3 mL/minute onto a MonoS column (8 ml) (Pharmacia, Inc., Piscataway, N.J.) equilibrated in Buffer C (50 mM of MES, pH 6.2, containing 6 mM of β-mercaptoethanol, 0.1 mM of EGTA, 1 µg/mL of leupeptin, 1 µg/mL of pepstatin A, and 1 mM of $MgCl_2$). PI 3-kinase was eluted with a linear gradient of 0–0.4M KCl in Buffer C over 120 minutes. In assaying fractions, two pools of PI 3-kinase activity were routinely found. The bulk of the activity was found in the flow-through, while about 20% of the activity was eluted in the gradient. Although the material in the gradient had considerable PI 4-kinase activity, essentially no PI 4-kinase activity was associated with the PI 3-kinase eluted in the flow-through. Therefore, the MonoS flow-through was concentrated by tangential flow filtration on a Mini-Ultrasette Omega 50 K membrane (Filtron, Inc., Northborough, Mass.) and diluted in Buffer C to lower the conductivity. The material was then reloaded onto the MonoS column using the above conditions. The PI 3-kinase bound to the column during the wash and was eluted in the gradient. Two pools of phosphatidylinositol kinase activity were obtained in the gradient; each was assayed for PI 3-kinase and PI 4-kinase activity. Pool I was found to contain 95% PI 3-kinase activity (and 5% PI 4-kinase) while Pool II contained predominantly PI 4-kinase activity.

Pool I from the MonoS column was diluted with Buffer A and chromatographed on MonoQ (1 ml) and eluted with a gradient of 0–0.4M KCl in Buffer A. The final pool was assayed for PI 3-kinase and PI 4-kinase activity. The final product was found to contain greater than 99% PI 3-kinase activity.

Assay of Purified PI-3 Kinase Activity

PI 3-kinase activity was measured as previously described by Matter, W. F., et al., *Biochemical and Biophysical Research Communications*, 186: 624–631 (1992). Inhibitor candidates were initially dissolved in DMSO and then diluted 10-fold with 50 mM of HEPES buffer, pH 7.5, containing 15 mM of $MgCl_2$ and 1 mM of EGTA. Ten microliters of this solution were incubated with purified bovine brain PI 3-kinase (9 µL) and phosphatidylinositol (5 µL of a 2 mg/mL stock solution in 50 mM of HEPES buffer, pH 7.5, containing 1 mM of EGTA). The final reaction mixture contained 0.1–5 ng/mL of inhibitor and 3% of DMSO (v:v). This concentration of DMSO had no effect on PI 3-kinase activity; control reaction mixtures contained 3% of DMSO (v:v) without inhibitor. Reactants were preincubated 10 minutes at ambient temperature and then the enzyme reaction was started upon addition of 1 µL [$\gamma$-$^{32}$P] ATP (2 mCi/mL, 500 µM of stock solution; 0.08 mCi/mL, 20 µM of final concentration; Dupont New England Nuclear, Boston, Mass.). The reaction was allowed to proceed for 10 minutes at ambient temperature with frequent mixing, after which time the reaction was quenched by addition of 40 µL of 1N HCl. Lipids were extracted with addition of 80 µL $CHCl_3$:MeOH (1:1, v:v). The samples were mixed and centrifuged, and the lower organic phase was applied to a silica gel TLC plate (EM Science, Gibbstown, N.J.), which was developed in $CHCl_3$:MeOH:$H_2O$:$NH_4OH$ (45:35:8.5:1.5, v:v). Plates were dried, and the kinase reaction visualized by autoradiography. The phosphatidylinositol 3-monophosphate region was scraped from the plate and quantitated using liquid scintillation spectroscopy with ReadyProtein (Beckman Instruments, Inc., Fullerton, Calif.) used as the scintillation cocktail. The level of inhibition for wortmannin and analogs was determined as the percentage of [$^{32}$P]-counts per minute compared to controls.

Alternatively, products of the PI 3-kinase reaction were confirmed by HPLC as discussed by Whitman, M., *Nature*, 332:644–646 (1988). Phospholipids were deacylated in methylamine reagent and separated using a Whatman Partisphere SAX anion exchange column as previously described by Auger, K. R., *Cell*, 57:167–175 (1989). A Radiomatic Model A-140 Flo-One/Beta on-line radioactivity detector was used to monitor the deacylated [$^{32}$P]-enzyme products; deacylated [$^3$H]PI 4-monophosphate was added as an internal standard.

Based on these experiments the following $IC_{50}$ values were obtained for inhibition of PI-3-kinase.

| Compound | $IC_{50}$ (ng/ml) |
|---|---|
| b | > 10 |
| c | 1.6 |
| d | > 10 |
| e | 0.38 |
| f | 10 |
| g | 0.6 |
| h | 0.4 |
| i (iA) | 1.2 (1.16) |
| j | 56.5 |
| k | 8.6 |
| l | 1.3 |
| m | 0.95 |
| n | 1.53 |

As can be seen from the above table, the compounds of this invention exhibit very potent activity as inhibiting agents of PI-3-kinase. Therefore, since PI-3-kinase activity has been linked to the formation and growth of various tumors, both benign and malignant, the compounds of this invention may also have usefulness as anti-tumor agents.

The present invention also provides for pharmaceutical formulations which include the above compounds and a pharmaceutically acceptable carrier, excipient or diluent. The following formulations are contemplated (active ingredient(s) refers to one of the wortmannin compounds of this invention):

Formulation 1

Hard gelatin capsules are prepared using the following ingredients:

| | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

| | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

| | Weight |
|---|---|
| Active ingredient | 0.25 |
| Ethanol | 29.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| Active ingredient(s) | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 mL |

Example 1

Preparation of Compound (b)

To a solution of 12.13 grams of wortmannin in 700 ml of methanol was added 70 ml of diethylamine. This mixture was stirred for 22 hours at room temperature, then evaporating under reduced pressure at room temperature to form the open ring compound (b).

Example 2

Preparation of 11-desacetyl wortmannin (Compound (f))

After evaporation, the crude solid of (b) was dissolved in 900 ml of dioxane followed by addition of 240 ml of 1N HCl stirred for 19 more hours. The mixture was concentrated under reduced pressure, then diluted with water, and the aqueous layer extracted with dichloromethane. The dichloromethane was dried over sodium sulfate and evaporated at room temperature under reduced pressure to yield 12.2 grams of crude Compound (f). This crude compound was purified by chromotography on silica eluting with 25% hexane in ethyl acetate. 7.35 grams (67% yield) of the title compound was obtained as a yellow glass. Analysis for $C_{21}H_{22}O_7$-calculated:-65.28;H-5.74;found: C-65.54;H-5.81.

Example 3

Preparation of 11-dimethylaminopropionyl-desacetyl- Wortmannin

To a solution of 252.9 mg of Compound (b) in 10 ml of anhydrous dichloromethane was added 480 μl of diisopropylethylamine followed by 223 μl of acryloyl chloride and stirred to room temperature for 3 hours. The solvent was evaporated under reduced pressure to yield a sticky orange solid. This crude material was cooled to 5° C. in an ice/acetone bath. Ice cold dimethylamine (5 ml) was added to the mixture and stirred at −5° C. for 1.25 hours. The mixture was allowed to warm at room temperature and the dimethylamine was distilled off. The residue was separated by chromatography on silica eluting with 10% methanol in dichloromethane, then 20% methanol in dichloromethane in a one-step gradient. Two UV active products were isolated and the product with the lower $R_f$ value was dissolved in 11 ml of dioxane and 2.3 ml of 1N HCl and the mixture stirred at room temperature for 20 hours. This mixture was diluted with ethyl acetate and washed with saturated sodium hydrogen carbonate. The organics were separated and combined, then washed with brine, dried with sodium sulfate, and evaporated at room temperature under reduced pressure. The crude product was purified by chromatography on silica, eluting with 7% methanol in dichloromethane. 37.4 mg of the title compound (14% yield) was isolated as a light orange solid.

Example 4

Preparation of 11-propionyl-desacetyl- Wortmannin

To a solution of 483.6 mg of compound (f) in 25 ml of pyridine was added 680 μl of propionic anhydride and the mixture stirred at room temperature for 26 hours. The mixture was evaporated at room temperature under reduced pressure and the residue purified by chromatography on silica, eluting with 50% hexane in ethyl acetate. This yielded 512.8 mg of the title compound (93% yield) as an off-white solid. Analysis for $C_{24}H_{26}O_8$-Calculated-C: 65.15;H:5.92;Found-C:65.07;H:5.96.

Example 5

Preparation of 11,17-desacetyl-dihydro Wortmannin 100 mg of compound (f) was reacted with 250 μl of 1M Borane in 3.5 ml of anhydrous tetrahydrofuran under a nitrogen atmosphere, was added 250 μl of 1M Borane, and the mixture stirred at 0° C. for 2.5 hours. The reaction was quenched by adding 1 ml of water at 0° C., then allowed to warm to room temperature, diluted with water and extracted with ethyl acetate. The ethyl acetate was washed with brine, dried with sodium sulfate and then washed and purified to yield 65.8 mg of the title compound (65% yield) as a white solid.

Example 6

Preparation of 11-propionyl-17-acetyl-desacetyl-dihydro-Wortmannin

To a solution of 104.9 mg of compound (e) produced in Example 13, in 5 ml of pyridine was added 95 μl of acetic anhydride. The mixture was stirred at room temperature for 27 hours. The mixture was then evaporated and the residue purified by chromatography on silica, eluting with 40% ethyl acetate in hexane to yield 89.9 mg of the title compound (77% yield) as a white solid. Analysis for $C_{26}H_{30}O_9$-Calculated-C: 64.19,H:6.22-Found-C:64.43;H:6.31.

The compounds prepared in Examples 7–14 were all prepared directly from compound (f), (11-desacetyl Wortmannin).

Example 7

Preparation of 11-phenylacetyl-desacetyl- Wortmannin

To a solution of 100.2 mg of (f) in 8 ml of anhydrous dichloromethane was added 150 μl of diisopropylethylamine followed by 120 μl of phenylacetyl chloride, and the mixture stirred for 23 hours. The mixture was diluted with dichloromethane and washed with saturated sodium hydrogen carbonate. The dichloromethane was washed with brine, dried with sodium sulfate and evaporated under reduced pressure to yield 214.6 mg of crude product which was purified by chromatography on silica, eluting with 50% hexane in ethyl acetate. 81.4 mg of the title compound (62% yield) was recovered as a light yellow glass.

Example 8

Preparation of 11-acrylyl-desacetyl- wortmannin 476.7 mg of compound (f) was reacted with acryloyl chloride as described in Example 7, and purified as described to yield 470 mg of the title compound (87% yield) as a light yellow solid. Analysis for $C_{24}H_{24}O_8$-Calculated-C:65.45;H: 5.49-Found-C:65.19;H-5.70.

Example 9

Preparation of 11-chloroacetyldesacetyl-Wortmannin 442.8 mg of compound (f) was reacted with chloroacetyl chloride as described in Example 7. After washing and purifying 200.1 mg of the title compound (38% yield) was obtained as a light beige solid. Analysis for $C_{23}H_{23}O_8Cl$-Calculated-C: 59.68;H:5.01-Found-C:59.66;H:5.06.

Example 10

Preparation of 11-isovaleryl-desacetyl-Wortmannin 479.9 mg of compound (f) was reacted with isovaleric chloride as described in Example 7. After washing and purifying, 350.3 mg of the title compound (60% yield) was obtained as a light orange solid.

Example 11

Preparation of 11-valeryl-desacetyl-Wortmannin 454.1 mg of compound (f) was reacted with valeric anhydride as described in Example 4, then purified to yield 517.7 mg of the title compound (93% yield) as a white solid. Analysis for $C_{26}H_{30}O_8$-Calculated-C:66.37;H:6.43-Found-C: 66.53;H:6.60.

Example 12

Preparation of 11-butyryl-desacetyl-Wortmannin 457.5 mg of compound (f) was reacted with butanyl anhydride as described in Example 4, then purified to yield 486.6 mg of the title compound (90% yield) as a white solid. Analysis for $C_{25}H_{28}O_8$-Calculated-C:65.78;H:6.18-Found-C: 65.52;H:6.38.

Example 13

Preparation of 11-propionyl-17-hydroxy-desacetyl-dihydro-Wortmannin

To an ice cold solution of 345 mg of compound (g) produced in Example 4 above, in 3.5 ml of anhydrous tetrahydrofuran under a nitrogen atmosphere, was added 250 µl of 1M Borane, and the mixture stirred at 0° C. for 2.5 hours. The reaction was quenched by adding 1 ml of water at 0° C., then allowed to warm to room temperature, diluted with water and extracted with ethyl acetate. The ethyl acetate was washed with brine, dried with sodium sulfate and evaporated and purified as above described to yield 309.9 mg of the title compound (89% yield) as a light yellow solid. Analysis for $C_{24}H_{28}O_8$:Calculated-C:64.85;H: 6.35-Found-C- 64.65;H-6.38.

Example 14

Preparation of 11-dehydro Wortmannin

To a solution of 401.1 mg of compound (f) in 25 ml of anhydrous dichloromethane was added 1.96 grams of pyridinium dichromate and the mixture stirred for 2.5 hours. The mixture was filtered through celite, and the celite washed with fresh dichloromethane. The dichloromethane was combined and evaporated at reduced pressure and the crude product purified by chromatography on silica, eluting with 50% hexane in ethyl acetate to yield 313.9 mg of the title compound (79% yield) as an off white solid. Analysis for $C_{21}H_{20}O_7$-Calculated-C: 65.62;H:5.24-Found-C:65.42;H:5.33.

The above examples are to be viewed only as potential methods of producing the compounds of this invention, and not as limiting of the compounds in any way. Other compounds of the general formula (I) may be produced utilizing one of the procedures outlined above and modifying that procedure in a well-known manner. It is foreseen that a person of ordinary skill in the art could easily produce any of the Formula (I) compounds by simply following one of the general schemes above.

We claim:

1. A compound of the formula:

(I)

[Structure of compound with substituents $CH_3O$, $R_1$, $CH_3$, $R_2$, $CH_3$, O, H, O, O, O]

wherein:

$R_1$ is $$\overset{O}{\underset{\|}{}},$$

or $OR_3$;

$R_2$ is $$\overset{O}{\underset{\|}{}},$$

or $OR_3$;

each $R_3$ individually is hydrogen, arylacyl, $C_3$–$C_8$ acyl or substituted acyl; and when $R_1$ is $$\overset{O}{\underset{\|}{}}$$

or OH, $R_2$ is not

2. The compound of claim 1 wherein:
$R_1$ is O-acyl and
$R_2$ is

O
‖ .

3. The compound of claim 1 wherein $R_1$ is $OR_3$.
4. The compound of claim 3 wherein $R_3$ is $C_3$–$C_8$ acyl or substituted acyl.
5. A compound of claim 1 having the general formula:

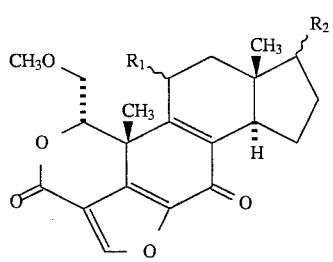

(Ia)

wherein $R_1$ is O-$C_3$–$C_8$ acyl, or a substituted derivative thereof; and
$R_2$ is

O
‖ .

6. The compound of claim 5 wherein $R_1$ is O-$C_3$–$C_8$ acyl.
7. A compound of claim 1 having the formula:

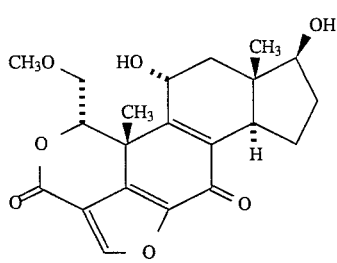

8. A compound of claim 1 having the formula:

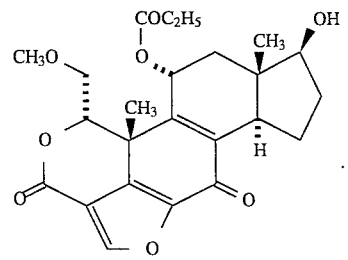

9. A compound of claim 1 having the formula:

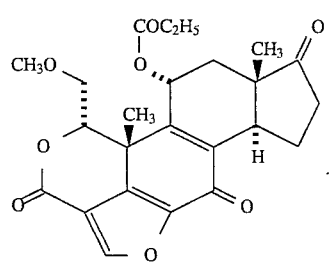

10. A compound of claim 1 having the formula:

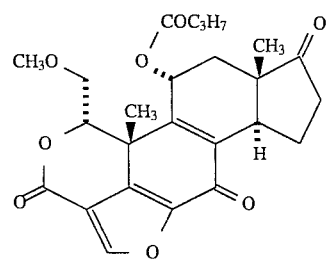

11. A compound of claim 1 having the formula:

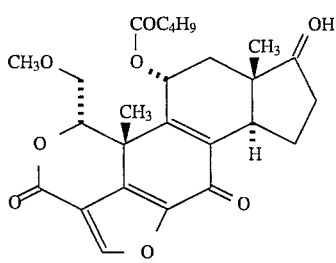

12. A compound of claim 1 having the formula:

13. A compound of claim 1 having the formula:

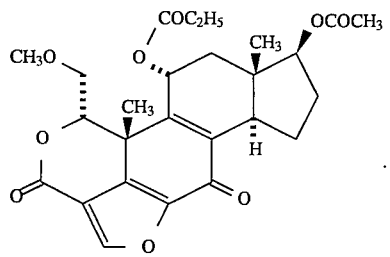

14. A compound of claim 1 having the formula:

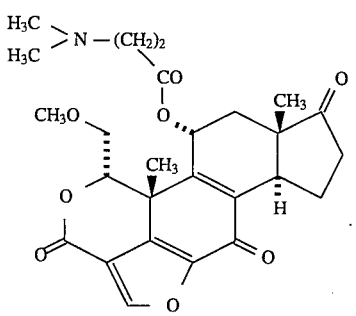

15. A compound of claim 1 having the formula:

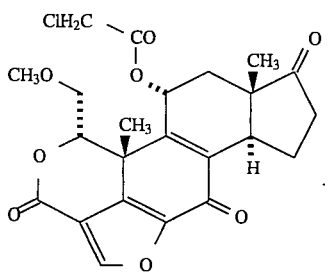

16. A compound of claim 1 having the formula:

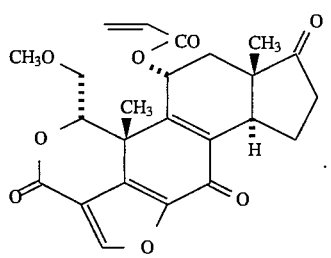

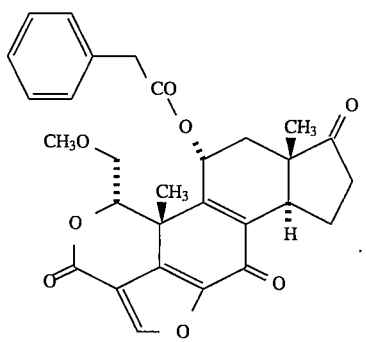

17. A method of inhibiting PI-3-kinase activity in mammals comprising administering to a mammal an effective amount of the compound of claim 1.

18. A method of inhibiting PI-3-kinase activity in mammals comprising administering to a mammal an effective amount of the compound of claim 5.

19. A method of inhibiting PI-3-kinase activity in mammals comprising administering to a mammal an effective amount of the compound of claim 7.

20. A method of inhibiting PI-3-kinase activity in mammals comprising administering to a mammal an effective amount of the compound of claim 8.

21. A method of inhibiting PI-3-kinase activity in mammals comprising administering to a mammal an effective amount of the compound of claim 9.

22. A method of inhibiting PI-3-kinase activity in mammals comprising administering to a mammal an effective amount of the compound of claim 10.

23. A method of inhibiting PI-3-kinase activity mammals comprising administering to a mammal an effective amount of the compound of claim 11.

24. A method of inhibiting PI-3-kinase activity mammals comprising administering to a mammal an effective amount of the compound of claim 12.

25. A method of inhibiting PI-3-kinase activity in mammals comprising administering to a mammal an effective amount of the compound of claim 13.

26. A method of inhibiting PI-3-kinase activity in mammals comprising administering to a mammal an effective amount of the compound of claim 14.

27. A method of inhibiting PI-3-kinase activity in mammals comprising administering to a mammal an effective amount of the compound of claim 15.

28. A method of inhibiting PI-3-kinase activity in mammals comprising administering to a mammal an effective amount of the compound of claim 16.

29. A method of inhibiting PI-3-kinase activity in mammals comprising administering to a mammal an effective amount of the compound of claim 5, and wherein $R_1$ is —OH.

30. A method of inhibiting PI-3-kinase activity in mammals comprising administering to a mammal an effective amount of the compound of claim 5 and wherein $R_1$ is $$\overset{O}{\underset{\|}{}}.$$

31. A pharmaceutical formulation comprising an effective amount of the compound of claim 1, and a pharmaceutically acceptable carrier, diluent, or excipient thereof.

32. A pharmaceutical formulation comprising an effective amount of the compound of claim 5, and a pharmaceutically acceptable carrier, diluent, or excipient thereof.

33. A pharmaceutical formulation comprising an effective amount of the compound of claim 6, and a pharmaceutically acceptable carrier, diluent, or excipient thereof.

34. A pharmaceutical formulation comprising an effective amount of the compound of claim 7, and a pharmaceutically acceptable carrier, diluent, or excipient thereof.

35. A pharmaceutical formulation comprising an effective amount of the compound of claim 8, and a pharmaceutically acceptable carrier, diluent, or excipient thereof.

* * * * *

UNITED STATES PATENT AND TRADEMARK OFFICE
CERTIFICATE OF CORRECTION

PATENT NO. : 5,480,906

DATED : January 2, 1996

INVENTOR(S) : Lawrence C. Creemer
Herbert A. Kirst

It is certified that an error appears in the above-identified patent and that said Letters Patent is hereby corrected as shown below:

In Scheme II, column 7, lines 5 to 15, structure (f) reads:

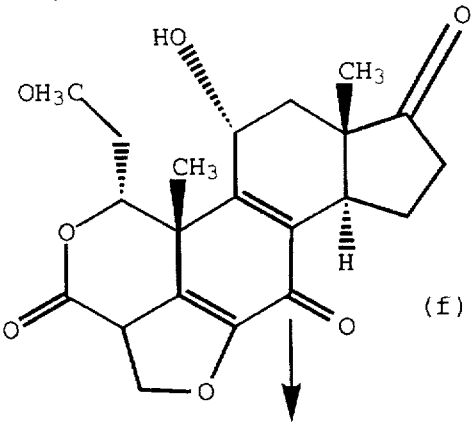

and it should be corrected to read:

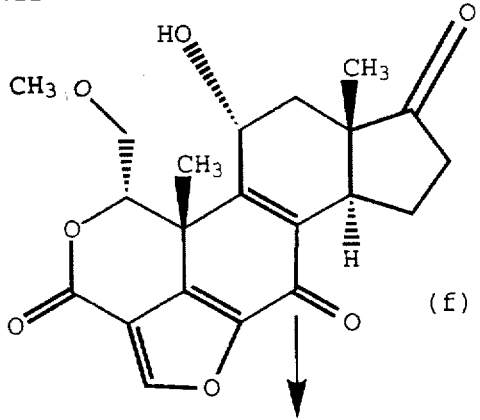

UNITED STATES PATENT AND TRADEMARK OFFICE
CERTIFICATE OF CORRECTION

Page 2 of 4

PATENT NO.    :    5,480,906

DATED         :    January 2, 1996

INVENTOR(S)   :    Lawrence C. Creemer
                   Herbert A. Kirst

It is certified that an error appears in the above-identified patent and that said Letters Patent is hereby corrected as shown below:

In Scheme II, column 7, lines 35 to 45, structure (d) reads:

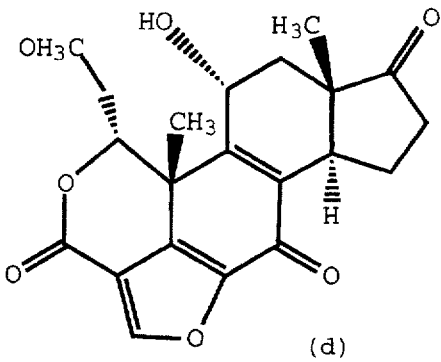

and it should be corrected to read:

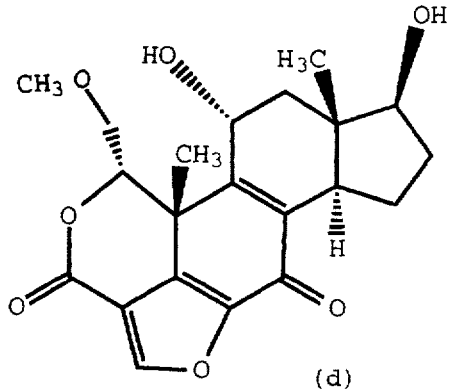

UNITED STATES PATENT AND TRADEMARK OFFICE
CERTIFICATE OF CORRECTION

PATENT NO.    :   5,480,906                          Page 3 of 4

DATED         :   January 2, 1996

INVENTOR(S)   :   Lawrence C. Creemer
                  Herbert A. Kirst

It is certified that an error appears in the above-identified patent and that said Letters Patent is hereby corrected as shown below:

In Scheme IIb, column 7, lines 48 to 58, structure (f) reads:

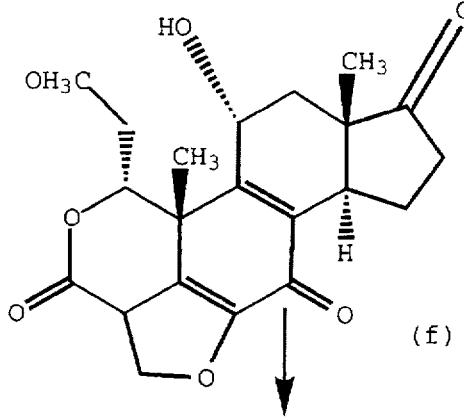

(f)

and it should be corrected to read:

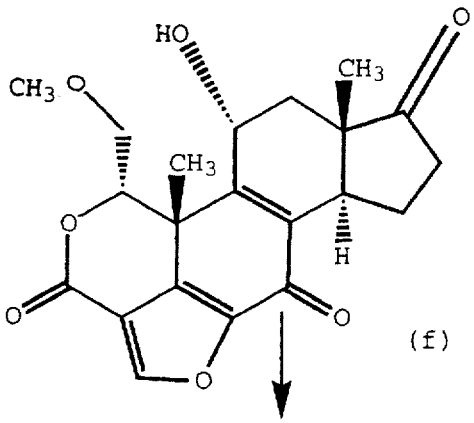

(f)

UNITED STATES PATENT AND TRADEMARK OFFICE
CERTIFICATE OF CORRECTION

PATENT NO.    : 5,480,906

DATED         : January 2, 1996

INVENTOR(S)   : Lawrence C. Creemer
                Herbert A. Kirst

It is certified that an error appears in the above-identified patent and that said Letters Patent is hereby corrected as shown below:

In Claim 11, the structure reads:

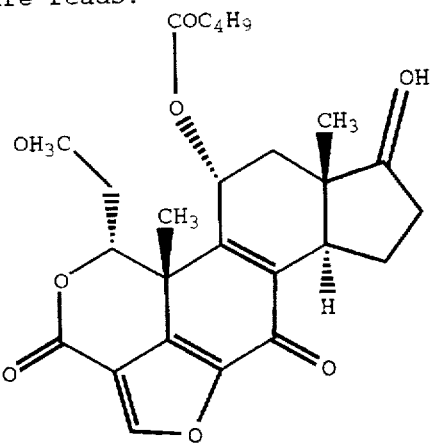

and it should be corrected to read:

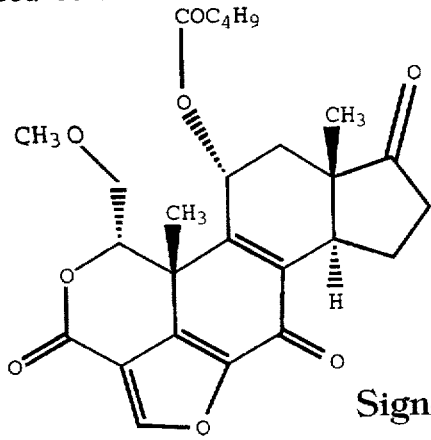

Signed and Sealed this

Fourth Day of November, 1997

*Attest:*

BRUCE LEHMAN

*Attesting Officer*    Commissioner of Patents and Trademarks